United States Patent
Padhye et al.

(10) Patent No.: US 10,365,290 B2
(45) Date of Patent: Jul. 30, 2019

(54) MULTIFUNCTIONAL PROTEIN MOLECULAR WEIGHT LADDERS

(71) Applicant: LI-COR, Inc., Lincoln, NE (US)

(72) Inventors: Nisha Padhye, Lincoln, NE (US); Rose Skopp, Lincoln, NE (US); Ying Wang, Lincoln, NE (US)

(73) Assignee: LI-COR, INC., Lincoln, NE (US)

(*) Notice: Subject to any disclaimer, the term of this patent is extended or adjusted under 35 U.S.C. 154(b) by 100 days.

(21) Appl. No.: 15/491,905

(22) Filed: Apr. 19, 2017

(65) Prior Publication Data

US 2017/0219613 A1 Aug. 3, 2017

Related U.S. Application Data

(62) Division of application No. 14/857,661, filed on Sep. 17, 2015, now Pat. No. 9,663,554.

(Continued)

(51) Int. Cl.
*C07K 7/06* (2006.01)
*G01N 33/58* (2006.01)
(Continued)

(52) U.S. Cl.
CPC .............. *G01N 33/96* (2013.01); *C07K 7/06* (2013.01); *C07K 14/795* (2013.01); *C12Q 1/28* (2013.01);
(Continued)

(58) Field of Classification Search
CPC ................. G01N 33/96; G01N 33/581; G01N 2333/908; G01N 2550/00; C07K 7/06
See application file for complete search history.

(56) References Cited

U.S. PATENT DOCUMENTS

| 5,316,908 A | 5/1994 | Carlson et al. |
| 6,455,261 B1 | 9/2002 | Wong et al. |

(Continued)

FOREIGN PATENT DOCUMENTS

| WO | 9830684 | 7/1998 |
| WO | 2011031497 | 3/2011 |

(Continued)

OTHER PUBLICATIONS

O'Reilly et al. The effect of solvent on the catalytic properties of microperoxidase-11. Phys. Chem. Chem. Phys. 2011, vol. 13, pp. 5304-5313. (Year: 2011).*

(Continued)

*Primary Examiner* — Shafiqul Haq
(74) *Attorney, Agent, or Firm* — Kilpatrick Townsend & Stockton LLP

(57) ABSTRACT

Multifunctional molecular weight protein ladders and methods of making thereof are disclosed herein that are useful for determining the molecular weight of a test protein and/or the relative mass or amount of the test protein in a protein separation assay, such as gel electrophoresis or western blotting. Also included are compounds of Formula I (e.g., mono acetylated MP-11 NHS ester) that may be used to label purified proteins of the protein ladder. The MP-11 label protein ladder can be detected on a blotting membrane by exposing the microperoxidase to a suitable substrate, such as a chromogenic substrate or a chemiluminescent substrate.

16 Claims, 5 Drawing Sheets

Step 1  Mono Acetylated MP-11 prepared from aqueous solution

Step 2  Mono Acetylated MP-11 NHS ester
Scheme 1 two steps synthesis of Mono N-acetylated MP-11 NHS ester

Related U.S. Application Data

(60) Provisional application No. 62/053,043, filed on Sep. 19, 2014.

(51) Int. Cl.
    *G01N 33/96*     (2006.01)
    *C07K 14/795*     (2006.01)
    *C12Q 1/28*     (2006.01)

(52) U.S. Cl.
    CPC ......... *G01N 33/581* (2013.01); *G01N 33/582* (2013.01); *G01N 2333/908* (2013.01); *G01N 2550/00* (2013.01)

(56) References Cited

U.S. PATENT DOCUMENTS

| | | |
|---|---|---|
| 6,995,274 B2 | 2/2006 | Lugade et al. |
| 7,005,518 B2 | 2/2006 | Peng et al. |
| 7,504,089 B2 | 3/2009 | Lugade et al. |
| 7,597,878 B2 | 10/2009 | Kovar et al. |
| 8,227,621 B2 | 7/2012 | Peng et al. |
| 8,303,936 B2 | 11/2012 | Draney et al. |
| 2003/0060647 A1 | 3/2003 | Talman et al. |
| 2005/0064537 A1 | 3/2005 | Ruggiero et al. |
| 2016/0084860 A1 | 3/2016 | Padhye et al. |

FOREIGN PATENT DOCUMENTS

| | | |
|---|---|---|
| WO | 2014004959 | 1/2014 |
| WO | 2016044619 | 3/2016 |

OTHER PUBLICATIONS

Marques et al., "Hemepeptide models for hemoproteins: the behavior of N-acetylmicroperoxidase-11 in aqueous solution", Journal of Inorganic Biochemistry, vol. 75, 1999, pp. 281-291.

Kadnikova et al., "Effects of the environment on microperoxidase-11 and on its catalytic activity in oxidation of organic sulfides to sulfoxides", Abstract only, J Org Chem., 2003, pp. 2600-2608.

International Search Report and Written Opinion dated Feb. 1, 2016 for PCT/US2015/050735, 10 pages.

Carraway et al., "Characterization of N-acetylated heme undecapeptide and some of its derivatives in aqueous media: Monomeric model systems for hemoproteins", Inorganic Chemistry, vol. 35, Issue 23, 1996, pp. 6885-6891.

Mentinova et al., "Solution Versus Gas-Phase Modification of Peptide Cations with NHS-Ester Reagents", Journal of The American Society for Mass Spectrometry, vol. 23, No. 2, Nov. 12, 2011, pp. 282-289.

O'Reilly et al., "The Effect of Solvent on the Catalytic Properties of Microperoxidase-11", Physical Chemistry Chemical Physics, vol. 13, No. 12, Jan. 1, 2011, pp. 5304-5313.

Zaitsu et al., "Heme-Undecapeptide Labeling on Insulin for the Immunoassay of Insulin with Chemiluminescence Detection", Analytical Sciences, The Japan Society for Analytical Chemistry, vol. 15, Sep. 1, 1999, pp. 871-878.

Bischof et al., "Heme Ladder, a Direct Molecular Weight Marker for Immunoblot Analysis," Analytical Biochemistry, vol. 409, No. 2, Feb. 1, 2011, pp. 213-219.

EP15842674.2, "Office Action," Feb. 11, 2019, 6 pages.

\* cited by examiner

Step 1 Mono Acetylated MP-11 prepared from aqueous solution

Step 2 Mono Acetylated MP-11 NHS ester

Scheme 1 two steps synthesis of Mono N-acetylated MP-11 NHS ester

Lane 1: sample stored at -80°C
Lanes 2 and 3: sample stored at room temperature for 2 days Light gray represents chemiluminescent signal.

MULTIFUNCTIONAL PROTEIN MOLECULAR WEIGHT LADDERS

CROSS-REFERENCE TO RELATED APPLICATIONS

The present application is a Divisional of U.S. Ser. No. 14/857,661 filed Sep. 17, 2015 (Allowed); which claims priority to U.S. Provisional Patent Application No. 62/053,043 filed Sep. 19, 2014; the full disclosures which are hereby incorporated by reference in their entirety for all purposes.

BACKGROUND OF THE INVENTION

A protein molecular weight marker or protein ladder can be used to identify the approximate size (molecular weight) or mass (amount) of a protein resolved by gel electrophoresis. As is recognized by those skilled in the art, the migration rate of a protein through a gel is inversely proportional to the protein's molecular weight.

There is a need in the field for protein ladders that can be visibly, fluorescently and chemiluminescently detected either simultaneously or sequentially. Additionally, simpler methods are needed for chemiluminescent systems that eliminate the need for the inclusion of antibodies with a catalytic function label to develop a chemiluminescence system.

Moreover, there is a need for improved methods of labeling a protein mixture, wherein the proteins are conjugated to multiple chemical moieties. The present invention satisfies these needs and provides other advantages as well.

BRIEF SUMMARY OF THE INVENTION

In one embodiment, the present invention provides a compound of Formula I:

wherein $R^1$, $R^2$, $R^3$, and $R^4$ are each members independently selected from the group consisting of hydrogen, an amine protecting group or L, wherein L is a linking group.

In a second embodiment, the present invention provides a protein standard comprising a plurality of purified proteins having differing molecular weight; and at least a first portion of the purified protein(s) is covalently labeled using a mono microperoxidase compound of Formula I (e.g., N-succinimidyl (NHS) ester at $R^4$). A "first portion" of the purified proteins can be one or more proteins.

In some aspects, the protein standard includes at least 5 different purified proteins. In other aspects, the protein standard includes at least 10 different purified proteins (1, 2, 3, 4, 5, 6, 7, 8, 9 10 or more). In some instances, the range of molecular weights of the protein standard is about 5 kDa to about 280 kDa. In other instances, the range of molecular weights of the protein standard is about 8 kDa to about 260 kDa. In some aspects, the protein ladder includes purified proteins or substantially purified proteins that are about 250 kDa, about 150 kDa, about 100 kDa, about 75 kDa, about 50 kDa, about 37 kDa, about 25 kDa, about 20 kDa, about 15 kDa, and about 10 kDa. In other aspects, the protein ladder includes purified proteins or substantially purified proteins that are about 250 kDa, about 130 kDa, about 100 kDa, about 70 kDa, about 55 kDa, about 35 kDa, about 25 kDa, about 15 kDa, and about 10 kDa. In some aspects, the protein ladder includes purified proteins or substantially purified proteins that are about 260 kDa, about 140 kDa, about 100 kDa, about 70 kDa, about 50 kDa, about 40 kDa, about 35 kDa, about 25 kDa, about 15 kDa, and about 10 kDa. In other aspects, the protein ladder includes purified proteins or substantially purified proteins that are about 260 kDa, about 160 kDa, about 90 kDa, about 70 kDa, about 50 kDa, about 38 kDa, about 30 kDa, about 25 kDa, about 15 kDa, and about 8 kDa. In another aspect, the protein ladder

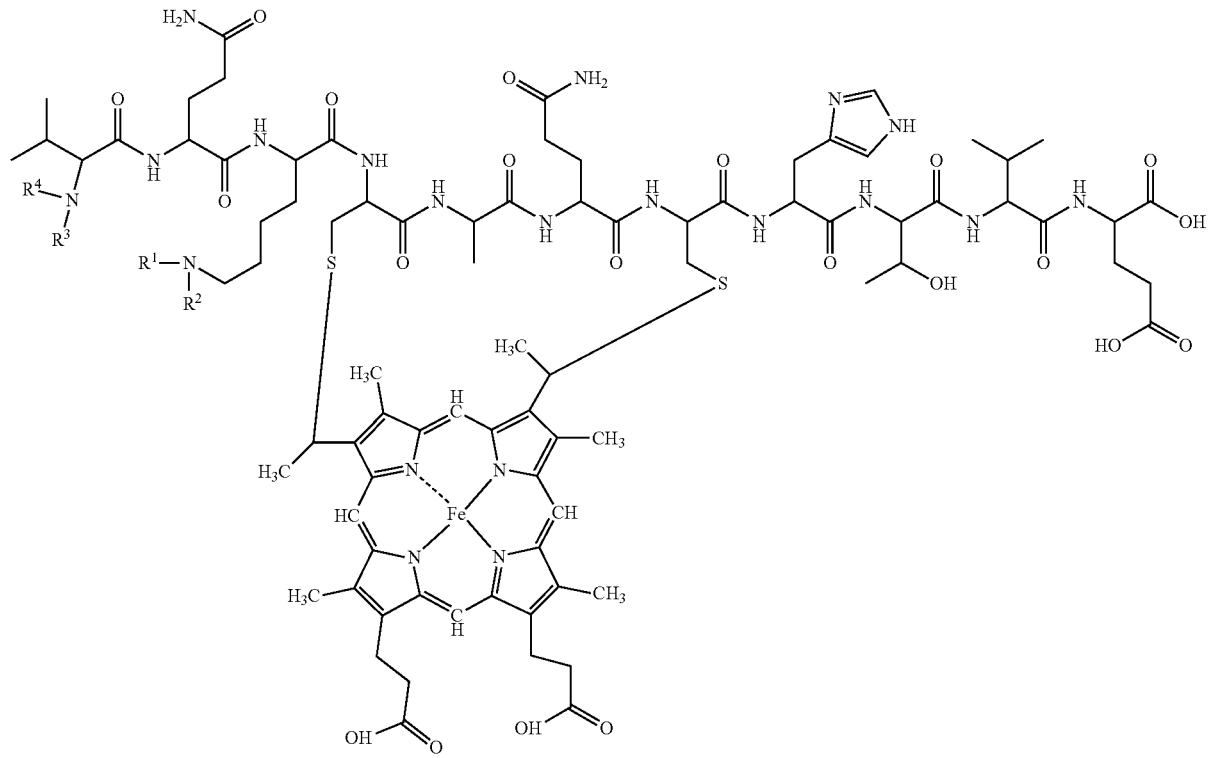

includes purified proteins or substantially purified proteins that are about 260 kDa, about 160 kDa, about 90 kDa, about 50 kDa, about 30 kDa, about 15 kDa, and about 8 kDa. In yet another aspect, the protein ladder includes purified proteins or substantially purified proteins that are about 260 kDa, about 125 kDa, about 70 kDa, about 38 kDa, about 25 kDa, and about 8 kDa.

In some aspects, at least 2 of the purified proteins of the protein standard are covalently labeled using a mono microperoxidase of Formula I. In other aspects, at least 3 of the purified proteins of the protein standard are covalently labeled using a mono microperoxidase of Formula I. In another aspect, at least 4 of the purified proteins of the protein standard are covalently labeled using a mono microperoxidase of Formula I. In some aspects, at least 5 of the purified proteins of the protein standard are covalently labeled using a mono microperoxidase of Formula I. In yet other aspects, at least 10 of the purified proteins of the protein standard are covalently labeled using a mono microperoxidase of Formula I.

In some aspects, at least a second portion of the purified proteins of the protein standard are labeled with an infrared (IR) fluorescent dye or porphyrin dye. In some instances, the IR fluorescent dye is a cyanine dye or a phthalocyanine dye. The cyanine dye may be IRDye® 800CW, IRDye 750, IRDye 680RD or IRDye 680LT (LI-COR, Lincoln, Nebr.). The phthalocyanine dye can be IRDye® 700DX (LI-COR, Lincoln, Nebr.). Those of skill in the art will know of other cyanine or phthalocyanine dyes useful for the present invention.

In some aspects, the first portion and the second portion of the purified proteins of the protein standard are the same purified proteins. In other aspects, the first portion and the second portion of the purified proteins of the protein standard are different purified protein(s).

In one aspect, the first portion of purified proteins of the protein standard is one or more proteins. The second portion of the purified proteins of the protein standard is one or more proteins. The one or more proteins of the first and second portion can be the same protein(s) or different protein(s).

In some aspects, at least a third portion of the purified proteins of the protein standard is labeled with a visible dye. In one aspect, the third portion of the purified proteins of the protein standard is one or more proteins. The one or more proteins of the first and second portion can be the same protein(s) or different protein(s) compared to the third portion of the purified proteins of the protein standard.

In a third embodiment, the present invention provides a kit for preparing a protein standard described herein. The kit includes a plurality of purified proteins of differing molecular weight, a mono microperoxidase NHS ester (or other functional labeling group), and a labeling buffer. In some aspects, a mono microperoxidase NHS ester is a mono MP-11 of Formula Ia:

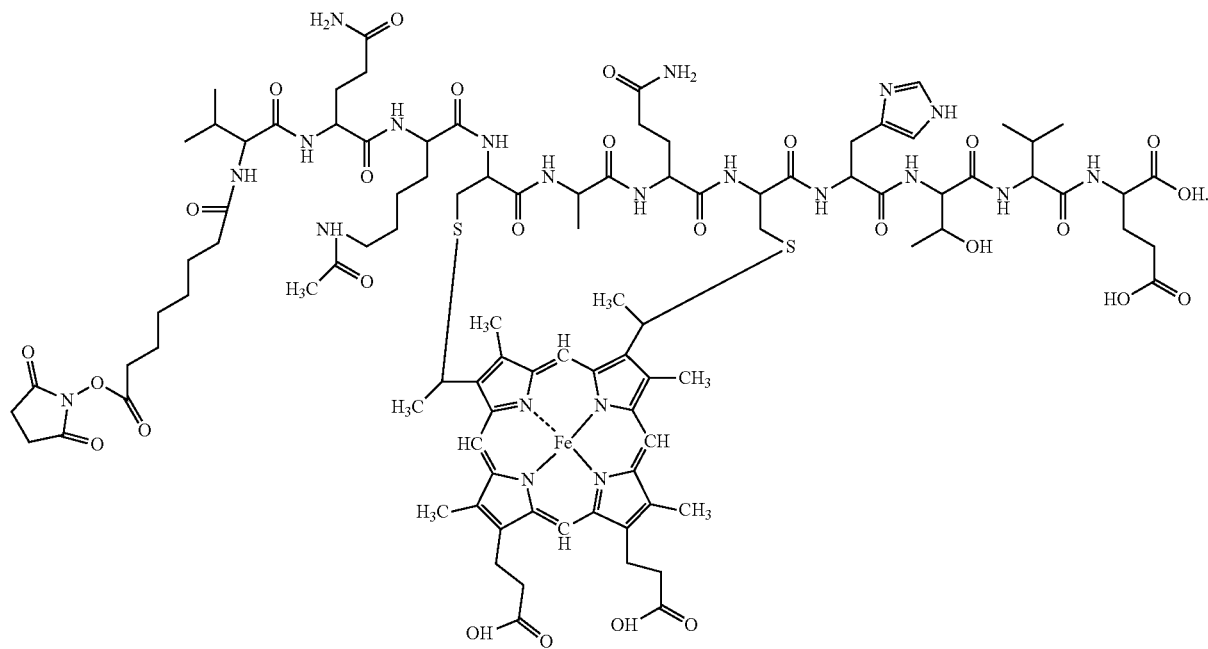

Ia

In some aspects, Formula Ia is a mixture of compounds wherein $R^1$, $R^2$, $R^3$, and $R^4$ are each members independently selected from hydrogen, an NHS ester and an acetyl group such as $R^1$ is acetyl, $R^2$ is hydrogen, $R^3$ is hydrogen and $R^4$ is an NHS ester (e.g., with 6 $CH_2$ groups with an amide linkage to the core). Alternatively, $R^1$ is an NHS ester and $R^3$ is an acetyl group. There can be a mixture of isomers such as between 1% to 99% of each of the isomers.

In some aspects, the labeling buffer is an amine-free buffer. In some aspects, the kit also includes a storage buffer. In preferred aspects, the storage buffer is substantially free of DTT, EDTA and $NaN_3$. In certain aspects, the kits are substantially free of antibodies possessing catalytic activity.

In a fourth embodiment, the present invention provides a method for preparing a multifunctional protein standard comprising a plurality of purified proteins labeled with at least two chemical moieties selected from the group consisting of a visible dye moiety, a catalytic moiety, a fluorescent dye moiety, and a combination thereof. The method includes (a) determining the optimum number of molar equivalents of the at least two chemical moieties based on the average molecular weight of the plurality of purified proteins when labeled individually; (b) preparing the plurality of purified proteins buffers amenable to the conjugation chemistries of at least two chemical moieties; and (c) incubating the at least two chemical moieties and the plurality of purified proteins under conditions such that the at least two chemical moieties covalently attach to the proteins to produce the multifunctional protein standard. In some aspects, the method also includes purifying the multifunctional protein standard. In some instances, the step of purifying the multifunctional protein standard comprises size exclusion chromatography, dialysis or both.

In some aspects, the step of incubating the at least two chemical moieties and the plurality of purified proteins comprises simultaneously conjugating the chemical moieties to the proteins. In other aspects, incubating the at least two chemical moieties and the plurality of purified proteins comprises sequentially conjugating the chemical moieties, wherein a chemical moiety with an NHS ester is conjugated to the proteins after a chemical moiety without an NHS ester. In yet other aspects, incubating the at least two chemical moieties and the plurality of purified proteins comprises sequentially conjugating the chemical moieties, wherein the order of conjugating is from the least to the most molar equivalents needed for each chemical moiety.

In some aspects, at least two purified proteins of the multifunctional protein standard are labeled with a catalytic moiety and a visible dye moiety using the method described herein. In other aspects, at least two purified proteins of the multifunctional protein standard are labeled with a catalytic moiety and a fluorescent dye moiety.

In preferred aspects, at least two purified proteins of the multifunctional protein standard are labeled with (i) a catalytic moiety, (ii) a visible dye moiety, (iii) a fluorescent dye moiety or any single or combination of the three, including (i) and (ii); (i) and (iii); (ii) and (iii); or (i), (ii), and (iii).

In some aspects, the step of incubating the at least two chemical moieties and the plurality of purified proteins includes (i) conjugating the visible dye moiety to the proteins, (ii) conjugating the fluorescent dye to the labeled proteins, and/or (iii) conjugating the catalytic moiety to the fluorescently labeled proteins. In some instances, the catalytic moiety is a mono microperoxidase NHS ester. In some aspects, the microperoxidase is a compound of Formula Ia:

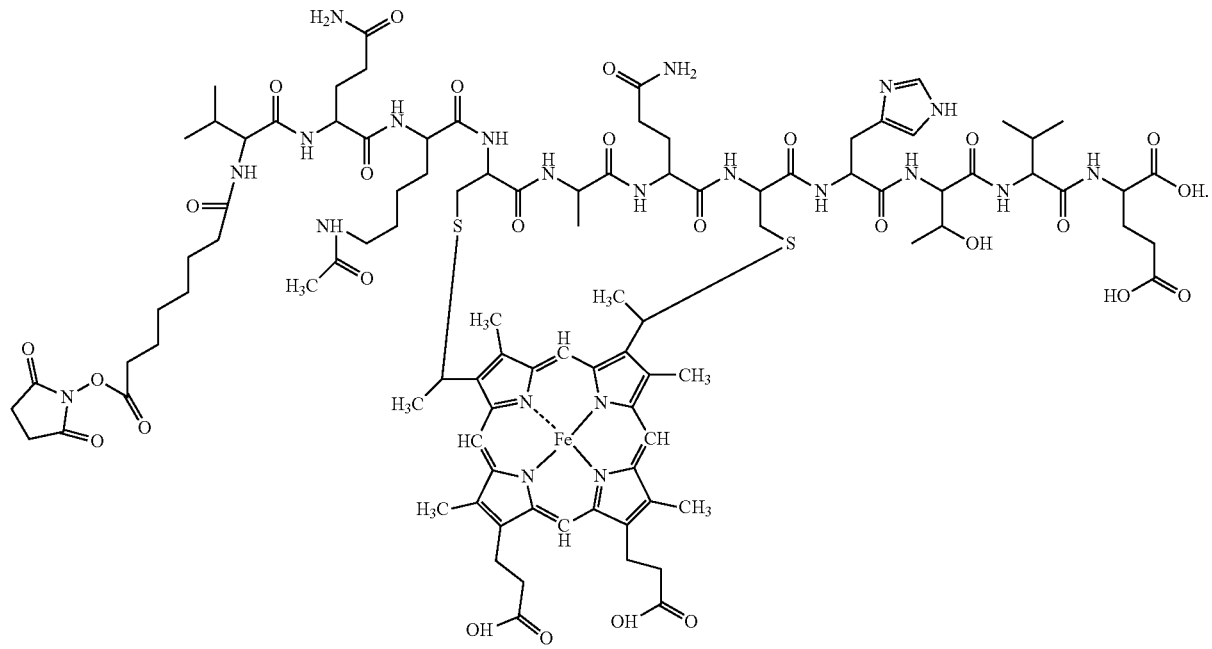

Ia

In some aspects, the fluorescent dye moiety is an infrared fluorescent dye or porphyrin dye. In some instances, the infrared fluorescent dye is a cyanine dye or a phthalocyanine dye. In some aspects, the cyanine dye is IRDye® 800CW, IRDye 750, IRDye 680RD, IRDye 650 or IRDye 680LT. In some aspects, the phthalocyanine dye is IRDye® 700DX.

In another aspect, the present invention provides a multifunctional protein standard prepared by any of the methods described herein.

In yet another embodiment, the present invention provides a method for performing a Western blot analysis, the method comprising:
(a) loading a protein standard comprising a plurality of purified proteins of differing molecular weight, wherein at least a first portion of the purified proteins is covalently labeled with a mono microperoxidase (MP) N-hydroxy succinimidyl (NHS) ester;
(b) electrophoresing the plurality of proteins to form a separated protein mixture;
(c) transferring the separated protein mixture to a membrane;
(d) adding a chemiluminescent substrate to form a chemi-signal; and
(e) capturing the chemi-signal with a film or an imager.

In some aspects, the membrane is nitrocellulose or PVDF. In some aspects, an unknown protein is loaded with the protein standard.

Other objects, features, and advantages of the present invention will be apparent to one of skill in the art from the following detailed description and figures.

BRIEF DESCRIPTION OF THE DRAWINGS

FIG. 4A shows a labeled, pre-stained protein ladder with MP-11 that was stored for 6 months. FIG. 4B shows a MP-11 labeled, pre-stained and IR dye conjugated protein ladder that was stored for 5 months at −80° C., −20° C. and 4° C.

DETAILED DESCRIPTION OF THE INVENTION

I. Introduction

Figure 1:
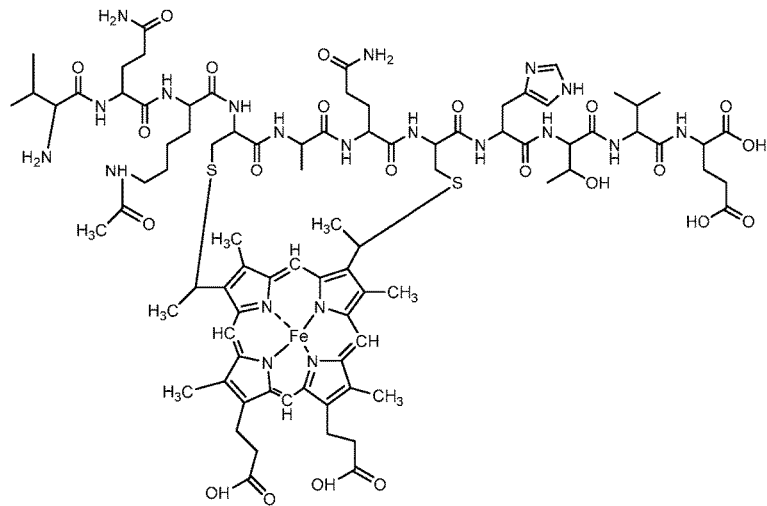
FIG. 1 illustrates a two-step method of synthesizing mono N-acetylated MP-11 NHS ester.
Figure 1:
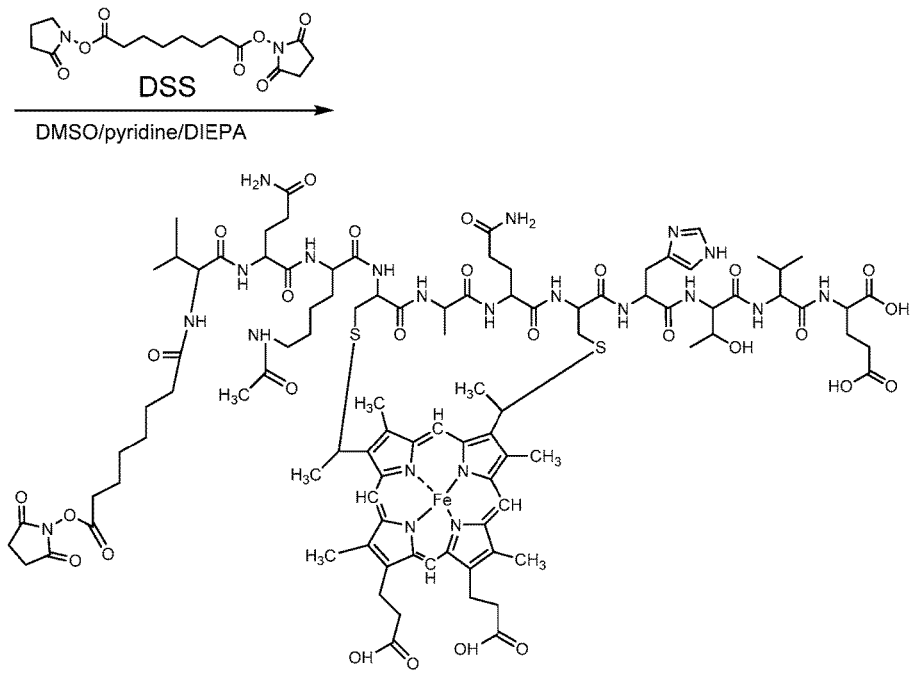

The present invention provides a multifunctional protein molecular weight ladder that is useful for visualization, production of chemiluminescence and infrared fluorescence in for example, a western blotting analysis. The invention provides methods that demonstrate the versatility of using the ladder in both chemiluminescent and fluorescent western blotting analysis. For instance, the molecular weight and the mass of a target protein can be estimated or determined using the protein standard described herein having at least one chemiluminescence reporter and at least one infrared fluorescence reporter (e.g., IRDye® fluorescent dye). Also provided herein is a method of making for example, an amino reactive mono microperoxidase that is useful for simultaneously labeling a plurality of proteins, such as pre-stained proteins of a molecular weight ladder. The present invention is also directed to labeling either subsequently or simultaneously such a catalytic protein ladder with one or more IR dyes such as near IR dyes. The invention is related to formulating a multifunctional protein molecular weight ladder that possesses up to three signal reporters in a buffer system that preserves (i) peroxidase-like activity, as well as (ii) visible and (iii) fluorescence properties of the ladder.

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "protein standard," "protein ladder," "molecular weight protein marker," "molecular weight marker," "protein molecular weight marker" refers to a plurality of purified proteins such as 1, 2, 3, 4, 5, 6, 7, 8, 9, 10, 11, 12, 13, 14, 15, 16, 17, 18, 19, 20 or more proteins that can separated according to molecular weight by protein electrophoresis and are useful for molecular weight estimation or determination.

The term "plurality of purified proteins" includes a quantity of at least two different full-length proteins or polypeptides, protein fragments (e.g., peptides), denatured proteins or proteins in their native state that have been purified or substantially purified, e.g., 2, 3, 4, 5, 6, 7, 8, 9, 10, 11, 12, 13, 14, 15 or more different full-length proteins or polypeptides, protein fragments, denatured proteins or proteins in their native state that have been purified. The plurality or mixture of purified proteins can be a mixture of full-length proteins or polypeptides, a mixture of protein fragments, a mixture of denatured proteins, a mixture of proteins in their native state, or any combination thereof.

The term "mono microperoxidase N-hydroxy succinimidyl ester," "mono microperoxidase NHS ester" or "microperoxidase NHS ester" refers to a heme containing peptide portion of cytochrome C that retains peroxidase activity and having a N-hydroxy succinimidyl (NETS) ester reactive group. Non-limiting examples of microperoxidases that are useful for the invention include MP-17 (having 17 amino acids), MP-9 (a nonapeptide), MP-8 (an octapeptide), and MP-6 (a hexapeptide). Any peptide derived from a peroxidase protein by proteolysis or synthesis and having a NETS ester group or other functional linking group can be used if the peptide possesses enzymatic activity or peroxidase activity.

The term "conjugating," "coupling" or "labeling" refers to linking of at least one chemical moiety to a protein by means of a suitable crosslinker capable of covalently binding the moiety to the protein.

The term "linking group" refers to a moiety on the compound that is capable of chemically reacting with a functional group on a different material (e.g., biomolecule) to form a linkage, such as a covalent linkage. See, e.g., R. Haughland, *The Handbook—A Guide to Fluorescent Probes and Labeling Technologies*, 9$^{th}$ Edition, Molecular Probes, Inc. (1992). Typically, the linking group is an electrophile or nucleophile that can form a covalent linkage through exposure to the corresponding functional group that is a nucleophile or electrophile, respectively. Alternatively, the linking group is a photoactivatable group, and becomes chemically reactive only after illumination with light of an appropriate wavelength. Typically, the conjugation reaction between the dye bearing the linking group and the material to be conjugated with the dye results in one or more atoms of the linking group being incorporated into a new linkage attaching the dye to the conjugated material.

The term "infrared fluorescent dye," "IR fluorescent dye" or "IR dye" or "NIR dye" refers to a dye having an absorption and emission wavelengths in the near-infrared spectrum of about 600-1000 nm. An infrared fluorescent dye can be detected using a near-infrared (NIR) fluorescence imaging system.

The term "cyanine dye" refers to a compound having two substituted or unsubstituted nitrogen-containing heterocyclic rings joined by an unsaturated bridge, such as a polymethine chain. Non-limiting examples of a cyanine dye, such as IRDye® 800CW are described in, e.g., U.S. Pat. Nos. 6,995,274; 7,504,089; 7,597,878; 8,227,621; and 8,303,936; the disclosures of which are herein incorporated by reference in their entirety for all purposes.

The term "phthalocyanine dye" refers to a silicon phthalocyanine dye that are useful for conjugating to a biomolecule, such as a protein. Non-limiting examples of a phthalocyanine dye, such as JRDye® 700DX are described in, e.g., U.S. Pat. No. 7,005,518, the disclosure of which is herein incorporated by reference in its entirety for all purposes.

The term "pre-stained protein standard" or "pre-stained protein ladder" refers to protein standards composed of proteins that are stained to allow for monitoring of the proteins during electrophoresis.

The term "chemical moiety" refers to a compound, chemical group, functional group or composition.

The term "visible dye moiety" or "visible dye" refers to a compound, chemical group, functional group, or composition that is visible to or can be detected by the unaided human eye.

The term "fluorescent dye moiety" or "fluorophore" refers that is inherently fluorescent. Fluorophores may contain substituents that alter the solubility, spectral properties or physical properties of the fluorophore. Numerous fluorophores are known to those skilled in the art and include, but are not limited to, coumarin, cyanine, benzofuran, a quinoline, a quinazolinone, an indole, a furan, a benzazole, a borapolyazaindacene and xanthenes including fluoroscein, rhodamine and rhodol as well as other fluorophores described in R. Haughland, *The Handbook—A Guide to Fluorescent Probes and Labeling Technologies*, 9$^{th}$ Edition, Molecular Probes, Inc. (1992).

The term "chemiluminescent moiety" or "chemiluminescent reagent" refer to a chemical moiety that can react with a substrate derived from luminol or an isomer thereof, including, but not limited to, luminal (3-aminophthalhydrazide) isoluminol (4-aminophthalhydrazide), ECL (Amersham), Clarity™ Western ECL substrate (Bio-Rad, Hercules, Calif.), SuperSignal (Thermo Fisher Scientific, Rockford, Ill.), or DuoLuX™ (Vector Laboratories, Burlingame, Calif.).

The term "optimum number of molar equivalents" refers to the number of individual chemical moieties which provide optimum individual functionalities on a protein. For example, the optimum molar equivalents of a visible dye produces a protein which has sufficient color to be seen by the unaided eye. The optimum molar equivalents of a fluorescent dye produces a protein that has sufficient fluorescent signal to be imaged on instruments such as LI-COR Oddysey Fc, Clx or Classic without saturating the detector or coalescing protein bands of different molecular weights. The optimum molar equivalents of a catalyst produce a protein that has sufficient chemiluminescent signal when incubated with an appropriate substrate and imaged on an instrument such as LI-COR Odyssey Fc or C-DiGit imager without saturating the detector, or without coalescing protein bands of different molecular weights. Optimal molar equivalents produce proteins which are sharp and well resolved when separated by SDS-PAGE.

III. Detailed Descriptions of Embodiments

A. Microperoxidase

Microperoxidases (MPs) are typically fragments of cytochrome C produced by enzymatic cleavage of the protein that results in segments of the cytochrome C amino acid chain with its heme group covalently attached via thioether bonds to the peptide. These small molecules have a molecular weight of less than 5,000 g/mol (5 kDa). Microperoxidases are catalytic and have peroxidative or peroxidase activity. Microperoxidases suitable for the present invention are commercially available. For example, MP-17, MP-11, MP-9, MP-8 and MP-6 are available from, e.g., Sigma-Aldrich Chemical Company, St. Louis, Mo. Combinations of microperoxidases are also useful.

Microperoxidases can be conjugated to one or more proteins in a protein ladder to produce a protein molecular weight ladder with catalytic activity. In fact, the catalytic activity is retained under electrophoresis and western blotting. The microperoxidase functionalized protein ladder can catalyze luminol-based chemical reactions to generate discrete chemiluminescent bands on western blot membranes. If the reagent is designed to be used with a peroxidase, it can be used with a microperoxidase.

Protein ladders without catalytic activity can be stored in a storage buffer containing Tris, EDTA, optionally SDS, NaN$_3$, glycerol and DTT. Prior to synthesizing a catalytic protein ladder, the storage buffer can be removed using standard methods, such as, but not limited to, utilizing a size exclusion column, e.g., spin column, and optionally, buffer exchange to a buffer compatible with the labeling reaction and also retain protein solubility by optionally adding SDS. In some aspects, the buffer comprises about 25 mM to about 100 mM sodium phosphate at about pH 8.5 with optionally 0.1%-1% SDS. In certain instances, SDS is included. In other instances, SDS is not included.

In one embodiment, the present invention provides a compound of Formula I:

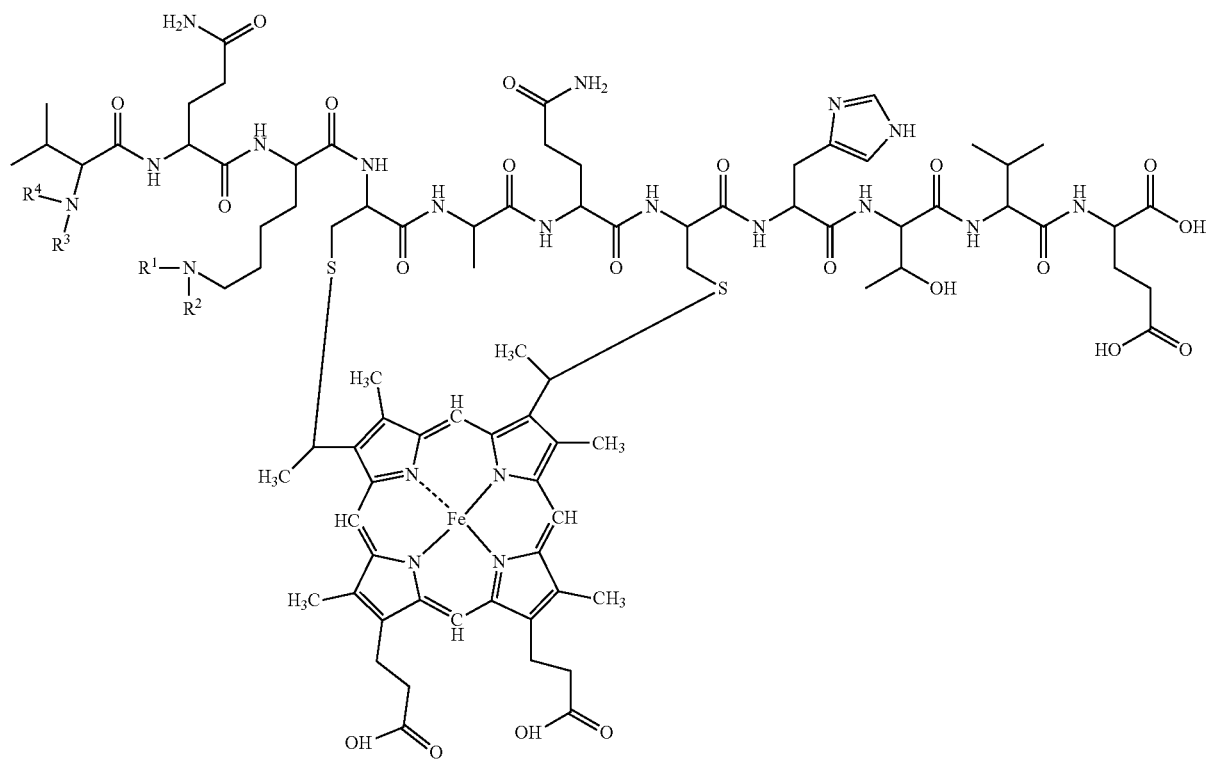

wherein $R^1$, $R^2$, $R^3$, and $R^4$ are each members independently selected from the group consisting of hydrogen, an amine protecting group or L, wherein L is a linking group.

Suitable amine protecting groups include, but are not limited to, an acetyl (Ac), a benzoyl (Bz), a benzyl (Bn) group, tert-butyloxycarbonyl (BOC) group, a carbamate group, a carbobenzyloxy (Cbz) group, 3,4-dimethoxybenzyl (DMPM), 9-fluorenylmethyloxycarbonyl (FMOC) group, p-methoxybenzyl carbonyl (Moz) group, p-methoxybenzyl (PMB), p-methoxyphenyl (PMP) group, or Tosyl (Ts) group. In one aspect, $R^1$ is $CH_3C(O)$ and $R^2$ is hydrogen.

Suitable linking groups L in Formula I are groups that can covalently react with an amine, hydroxyl, or sulfhydryl for bioconjugation, crosslinking, labeling and/or immobilization. These groups can be, for example, an NHS ester, a sulfo-NHS ester, N-maleimide, N-succinimide, or hydrazide moieties.

For example, N-Hydroxysuccinimide (NETS) is an organic compound with the formula $C_4H_5NO_3$. NETS is used as an activating reagent for carboxylic acids. For example, activated acids (basically esters with a good leaving group) can react with amines on proteins to form amides. In formula I, any of $R^1$-$R^4$ can be an NETS ester, wherein the NETS ester is linked to the microperoxidase via a methylene(s) group and an amide bond. The number of methylene(s) can be 1-20, such as 1, 2, 3, 4, 5, 6, 7, 8, 9, 10, 11, 12, 13, 14, 15, 16, 17, 18, 19, 20 or more (see, FIG. 1, step 2, with DSS (disuccinimidyl suberate)). The methylene groups can be optionally interrupted with heteroatoms. A sulfo-NHS can be used to increase water solubility.

An N-maleimide is a chemical compound with the formula $H_2C_2(CO)_2NH$, wherein the hydrogen on the nitrogen is replace with an amine or sulfhydryl group on a protein. Other groups include, but are not limited to, isothiocyanates, isocyanates, acyl azides, sulfonyl chlorides, aldehydes, glyoxals, epoxides, oxiranes, carbonates, aryl halides, imidoesters, carbodiimides, anhydrides, and fluorophenyl esters. Most of these conjugate to amines on proteins by either an acylation or an alkylation reaction.

In certain aspects, the compound of Formula I can be conjugated to proteins using conjugation chemistry well known in the art. For example, an activated ester (an NETS ester) can react with a primary amine to make a stable amide bond. A maleimide on Formula I and a thiol group on a protein can react together to make a thioether. Alkyl halides on Formula I react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for conjugation. For example, a free amino group on the MP can be conjugated to a protein via glutaraldehyde cross-linking, or via carbodiimide cross-linking to available carboxy moieties on the protein. Also, a protein with a free sulfhydryl group can be conjugated to a MP via maleimide activation, e.g., using sulfosuccinimidyl-4-(N-maleimidomethyl)cyclohexane-1-carboxylate (Sulfo-SMCC), then linkage to the sulfhydryl group.

In certain instances, "L" is "$L^c$" which is a covalent link between an MP such as MP-11 and a protein. In certain aspects, $L^c$ comprises a covalent bond from column "C" in Table 1 between an MP and a protein. In other words, $L^c$ is the resulting bond between an MP having a reactive functional group and a protein. $L^c$ can be for example, an amide, a thioether, or an alkylamine.

Methods for individually conjugating a protein are known to those skilled in the art, such as methods using reagents containing N-maleimide, N-succinimide, or hydrazide moieties that selectively react with sulfhydryl groups, amino groups or aldehyde groups, respectively. N-succinimide modified MP-11 conjugation can be performed at any of the four carboxyl or two amino groups of MP-11. However, crosslinking between MP-11 and the protein ladder may occur such that the discrete bands of the ladder do not appear on western blotting. Thus, blocking the carboxyl and/or amino groups is sometimes useful to synthesize a MP-11 having NHS ester functionality.

Selected examples of reactive functionalities useful for attaching a compound of Formula I to proteins are shown in Table 1, wherein the bond results from the reaction of a compound of Formula I with a protein. Column A of Table 1 is a list of the reactive functionalities, which can be on the compound of Formula I or the protein. Column B is a list of the complementary reactive groups (preferably, a carboxyl, hydroxyl, thiol, or amino functionality), which can be on the protein or the compound of Formula I, and which react with the indicated functionality of Column A to form the bond of Column C. Those of skill in the art will know of other bonds suitable for use in the present invention.

TABLE 1

Exemplary Bonds for Linking Groups

| A<br>Reactive Functionality<br>(Compound of Formula I or protein) | B<br>Complementary Group<br>(protein or Compound of Formula I) | C<br>Resulting Linking Group |
|---|---|---|
| activated esters* | amines/anilines | amides |
| acrylamides | thiols | thioethers |
| acyl azides** | amines/anilines | amides |
| acyl halides | amines/anilines | amides |
| acyl halides | alcohols/phenols | esters |
| acyl nitriles | alcohols/phenols | esters |
| acyl nitriles | amines/anilines | amides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |
| anhydrides | amines/anilines | amides/imides |
| aryl halides | thiols | thiophenols |
| aryl halides | amines | aryl amines |
| azides | alkynes | 1,2,3-triazoles |
| aziridines | thiols | thioethers |
| boronates | glycols | boronate esters |
| activated carboxylic acids | amines/anilines | amides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| epoxides | thiols (amines) | thioethers (alkyl amines) |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonyl halides | amines/anilines | sulfonamides |

*Activated esters, as understood in the art, generally have the formula —C(O)OM, where —OM is a leaving group (e.g. succinimidyloxy (—OC$_4$H$_4$NO$_2$), sulfosuccinimidyloxy (—OC$_4$H$_3$NO$_2$SO$_3$H), -1-oxybenzotriazolyl (—OC$_6$H$_4$N$_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or —C(O)OM is a carboxylic acid activated by a carbodiimide to form an anhydride or mixed anhydride —C(O)OC(O)R$^a$ or —C(O)OC(NR$^a$)NHR$^b$, wherein R$^a$ and R$^b$ are members independently selected from the group consisting of C$_1$-C$_6$ alkyl, C$_1$-C$_6$ perfluoroalkyl, C$_1$-C$_6$ alkoxy, cyclohexyl, 3-dimethylaminopropyl, or N-morpholinoethyl).
**Acyl azides can also rearrange to isocyanates.

In one aspect, the L in Formula I is an N-succinimide ester with between 2 and 12 methylene groups (such as 2, 3, 4, 5, 6, 7, 8, 9, 10, 11, or 12 CH$_2$ groups) with an amide linkage to a MP (e.g. MP-11). In other instances, L is a member selected from the group of a direct link, or a covalent linkage, wherein said covalent linkage is linear or branched, cyclic or heterocyclic, saturated or unsaturated, having 1-60 atoms selected from the group consisting of C, N, P, O, and S, wherein L can have additional hydrogen atoms to fill valences, wherein said linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds.

In other instances, L is a member selected from the group consisting of a PEG, a block copolymer of PEG-polyurethane and a PEG-polypropylene.

In other instances, L is a member selected from the group consisting of a polysaccharide, a polypeptide, an oligosaccharide, a polymer, a co-polymer and an oligonucleotide.

In other instances, L is of the formula:

$$-X^1-Y^1-X^2-$$

wherein:

X$^1$ is a member selected from the group consisting of a bivalent radical, a direct link, oxygen, an optionally substituted nitrogen and sulfur;

Y$^1$ is a member selected from the group consisting of a direct link and C$_1$-C$_{10}$ alkylene optionally interrupted by a heteroatom; and X$^2$ is a member selected from the group consisting of a bivalent radical, a direct link, oxygen, an optionally substituted nitrogen and sulfur.

L$^c$ is the resulting bond between L and a protein. Typically, L contains a reactive group which reacts with an amino, a sulfhydryl, a hydroxyl, or a carboxyl group of a protein and forms L$^c$. (See, Table 1.)

In one aspect, Formula I is Formula Ia:

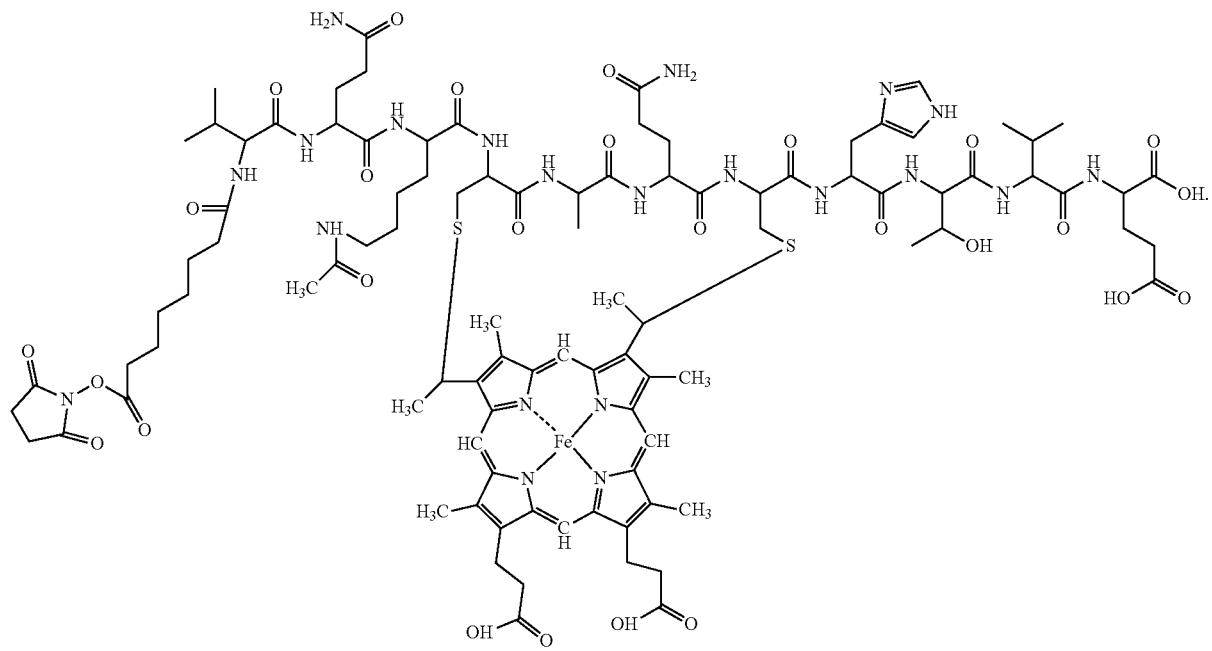

Ia

Microperoxidase-11 (e.g., MP-11) is prone to aggregation in solution, via axial ligation and intermolecular interactions (Kadnikova and Kostić, *J Org Chem,* 2003, 68(7):2600-8). The present invention is based, in part, on the surprising discovery of a two-step synthesis reaction for the production of a mono MP-11 NHS ester (Formula I). First, to eliminate MP-11 aggregation, the first primary amino group of the microperoxidase can be blocked using a reagent with an amino reactive group including, but not limited to, isothiocyanates, isocyanates, acyl-azides or a derivative thereof. The blocking reaction can be performed in an aqueous solution with any water-soluble mono NHS ester. In some aspects, the blocking reagent is sulfosuccinimidyl acetate (sulfo-NHS-acetate) in an aqueous solution, such as a phosphate buffer at about pH 8.5. The reaction when performed with low levels of MP-11 and stepwise added sulfosuccinimidyl acetate into reaction can also improve the yield of Mono-acetyl MP-11. A less than or equal to 1 mg/ml of MP-11 was used for reducing MP-11 aggregation and di-acetyl MP-11 as well. After the blocking reaction, the resulting Mono N-acetylated MP-11 can be purified using an acid, such as an acid having a pH of about pH 2-5.

MP-11 is insoluble (e.g., completely insoluble) in organic solvents. Yet, an amino blocked MP-11 (e.g., an N-acetylated MP-11) has increased solubility in organic solvents and can be reacted with a water-insoluble crosslinker, such as a homobifunctional NHS ester.

In the second step of the synthesis reaction, standard NHS chemistry can be used to label the modified MP-11. In some aspects, the acetylated MP-11 is reacted in an organic solvent, e.g., anhydrous dimethyl sulfoxide (DMSO) to a water-insoluble homobifunctional NHS ester, e.g., disuccinimidyl suberate (DSS). In other aspects, the acetylated MP-11 is dissolved in pyridine and admixed with the crosslinker solution that can contain N,N-diisopropylethylamine (DIPEA).

The NHS ester (or succinimidyl ester) of microperoxidase MP-11 can be used to conjugate MP-11 to the primary amines (R—NH$_2$) of purified proteins. The conjugation forms an amide bond between MP-11 and the protein. It can react with non-protonated aliphatic amine groups, including the amine terminus and the ε-amino group of lysines of the protein.

B. Multifunctional Protein Ladders

The compositions and methods of the present invention provide a protein molecular weight ladder comprising multiple purified proteins that are labeled with at least one microperoxide (e.g., MP-11) moiety and either at least one visible dye, at least one fluorescent dye, or both dyes. In some aspects, at least one protein is labeled with both the MP-11 moiety and a visible dye. For instance, the protein can be selectively labeled with a visible dye on a first amino acid and labeled with MP-11 at a different amino acid. In other aspects, at least one protein is labeled with both the MP-11 moiety and a fluorescent dye. For instance, the protein can be selectively labeled with a fluorescent dye on a first amino acid and labeled with MP-11 at a different amino acid. In yet other aspects, at least one protein is labeled with (i) the MP-11 moiety, (ii) a visible dye, and (iii) a fluorescent dye. For instance, the protein can be selectively labeled with a visible dye on a first amino acid, labeled with MP-11 at a second amino acid, and labeled with a fluorescent dye at a third amino acid.

In some aspects, the molecular weight standard includes 2, 3, 4, 5, 6, 7, 8, 9, 10, 11, 12, 13, 14, 15 or more different, labeled proteins in which 1, 2, 3, 4, 5, 6, 7, 8, 9, 10, 11, 12, 13, 14, 15 or more proteins are selectively labeled with at least one MP-11 moiety on a first amino acid and selectively labeled with at least one visible dye on a second amino acid. In other aspects, the molecular weight standard includes 2, 3, 4, 5, 6, 7, 8, 9, 10, 11, 12, 13, 14, 15 or more different, labeled proteins in which 1, 2, 3, 4, 5, 6, 7, 8, 9, 10, 11, 12, 13, 14, 15 or more proteins are selectively labeled with at least one MP-11 moiety on a first amino acid and selectively labeled with at least one fluorescent dye on a second amino acid. In yet other aspects, the molecular weight standard includes 2, 3, 4, 5, 6, 7, 8, 9, 10, 11, 12, 13, 14, 15 or more different, labeled proteins in which 1, 2, 3, 4, 5, 6, 7, 8, 9, 10, 11, 12, 13, 14, 15 or more proteins are selectively labeled with at least one MP-11 moiety on a first amino acid, selectively labeled with at least one visible dye on a second amino acid, and selectively labeled with at least one fluorescent dye on a third amino acid. Optionally, 2, 3, 4, 5, 6, 7, 8, 9, 10, 11, 12, 13, 14, 15 or more labeled proteins of the protein standard can be selectively labeled with a different fluorescent dye on a fourth amino acid, such that the protein is labeled with two different fluorescent dyes with different excitation/emission wavelengths.

The protein standard described herein can span a molecular weight range of from about 1 kDa to about 500 kDa or more, from about 1 kDa to about 300 kDa or more, from about 1 kDa to about 250 kDa or more, from about 1 kDa to about 200 kDa or more, from about 5 kDa to about 300 kDa or more, from about 5 kDa to about 250 kDa or more, from about 8 kDa to about 260 kDa or more, from about 10 kDa to about 200 kDa or more, from about 10 kDa to about 150 kDa or more, from about 10 kDa to about 100 kDa or more, from about 10 kDa or less to about 150 kDa, or from about 10 kDa or less to 300 kDa.

In some aspects, the protein standard includes 3, 4, 5, 6, 7, 8, 9, 10, 11, 12, 13, 14, 15, or more labeled proteins that differ in size from one another by an increment of about 5 kDa, 10 kDa, 15 kDa, 20 kDa, 25 kDa, 30 kDa, 35 kDa, 40 kDa, 45 kDa, 50 kDa, 55 kDa. 60 kDa, 65 kDa, 70 kDa, 75 kDa, 80 kDa, 85 kDa, 90 kDa, 95 kDa, 100 kDa, 105 kDa, 110 kDa, 115 kDa, 120 kDa, 125 kDa, 130 kDa, 135 kDa, 140 kDa, 145 kDa, 150 kDa, 155 kDa, 160 kDa, 165 kDa, 1700 kDa, 175 kDa, 180 kDa, 185 kDa, 190 kDa, 195 kDa, 200 kDa, 205 kDa, 210 kDa, 215 kDa, 220 kDa, 225 kDa, 230 kDa, 235 kDa, 240 kDa, 245 kDa, 250 kDa, 255 kDa. 260 kDa, 265 kDa, 270 kDa, 275 kDa, 280 kDa, 285 kDa, 290 kDa, 295 kDa or more.

In some aspects, the dual functional protein ladder having catalytic and fluorescent activity (e.g., IR fluorescent activity) can be mixed with a pre-stained protein ladder. The dual functional protein ladder and the pre-stained ladder can contain one or more purified proteins of the same molecular weight. Alternatively, the dual functional protein ladder and the pre-stained ladder can contain one or more purified proteins of different molecular weights. In some aspects, the purified proteins of the dual functional protein ladder and the pre-stained protein ladder are the same molecular weights and/or have the same mass.

In other aspects, the dual functional protein ladder having catalytic activity and pre-stained proteins can be mixed with a IR fluorescent protein ladder. The dual functional protein ladder and the IR fluorescent protein ladder can contain one or more purified proteins of the same molecular weight. Alternatively, the dual functional protein ladder and the IR fluorescent protein ladder can contain one or more purified proteins of different molecular weights. In some aspects, the purified proteins of the dual functional protein ladder and the IR fluorescent protein ladder are the same molecular weights and/or have the same mass.

The purified proteins of the protein standard can be purified from naturally occurring sources. Alternatively, the proteins can be expressed recombinantly according to standard methods recognized by those skilled in the art. The proteins can also be chemically synthesized according to standard methods.

The multifunctional protein molecular weight ladder described herein has sustainable and long-lived peroxidase-like activity. Such a protein ladder is versatile and suitable for using to estimate (e.g., determine) molecular weights in multiplex protein detection assays that measure chemiluminescence and fluorescence simultaneously or sequentially.

C. Methods of Labeling Pre-Stained Molecular Weight Protein Ladders Using for Example, a Mono MP-11 NHS Ester Described herein is a method where a mixture of proteins, e.g., protein markers, standards, or a protein ladder, can be conjugated to moieties which contain visible color, catalytic activity, fluorescent activity, and any combination thereof. The conjugation process uses the novel idea of mean molecular weight ("mean MW") of the proteins in the mixture to achieve consistent and reproducible conjugation across the molecular weight range of the proteins in the mix. For example, in a mixture of 8 proteins of molecular weight 250 kDa, 130 kDa, 80 kDa, 50 kDa, 37 kDa, 25 kDa, 15 kDa, and 10 kDa, the mean molecular weight of the mixture is 74.6 kDa. The mean MW is used to calculate the estimated molar concentration of the protein mixture. Depending on the moiety(s) to be conjugated, 1-40 molar equivalents of material are added to the labeling/conjugation reaction simultaneously or step wise (e.g. sequentially). In some aspects, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 molar equivalents of MP-11 or other microperoxidase, the visible dye or the fluorescent dye is used in the reaction.

The optimal number of equivalents is determined by the ultimate functionality of the moiety in the mixture. The number of molar equivalents used in the labeling reaction may be determined empirically. For example, robust chemiluminescent activity requires labeling using 30 molar equivalents of catalyst to provide a chemiluminescent signal from a variety of substrates using film or digital imagers such as Odyssey Fc or C-Digit imager. For fluorescent dyes, optimal fluorescence signal can be achieved by using e.g. 4-8 molar equivalents of dye. For visible dyes, optimal color or visible signal can be achieved using e.g. 8-16 equivalents of dye. The optimal number or molar equivalents depends on the desired functionality of the moiety in the protein mixture.

Up to three moieties or functionalities, e.g., 1, 2 or 3 functionalities can be conjugated to a portion of proteins in a mixture. The first conjugation may label a portion of proteins with one or more visible dyes. A second functionality may be the addition of a fluorescent dye. A third functionality may be the addition of a catalytic moiety which functions as an enzyme analog.

In one embodiment, a visible dye label is applied first to the protein(s). The second labeling can be to a fluorescent dye where the number of molecules to be conjugated to each protein is relatively small. The third functionality to be added can be a catalytic moiety (e.g., MP-11) which introduces a relatively large number of molecules to provide chemiluminescent functionality. An example of this would be MP-11 NHS ester labeling. After the addition of any moiety which does not utilize NHS ester chemistry, e.g., visible dye, the order of the moiety addition should follow from least to most molar equivalents needed to provide the desired functionality.

When the conjugation between the moiety and protein mixture utilizes a reactive NHS ester to covalently attach the moiety to the proteins, the labeling is performed in an amine-free buffer such as 50 mM sodium phosphate, pH 7.7-9.0 or 50 mM sodium phosphate, pH 7.7-9.0 for two-four hours at ambient temperature. Optimization of the labeling parameters can be required. First, the optimum number of molar equivalents of each moiety based on the average molecular weight of the protein mix when added individually to the labeling reaction is determined. Next, the protein mixture is prepared in a buffer that is amenable to the conjugation chemistry. Then, the moiety is added to the mixture and incubated to allow the covalent attachment of the moiety to the proteins in the mix. The final step includes the removal any unreacted moieties using commonly used protein purification techniques, such as size exclusion chromatography or dialysis with appropriate molecular weight cutoff limits.

Alternatively, the conjugation can be performed in a one pot (one reaction vessel) reaction if the labeling conditions for each moiety are similar. As described above, the initial step includes determining the number of molar equivalents of each moiety to be added by optimizing individual labeling of the protein mix. Next, a cocktail of the moieties in pre-determined ratios is prepared. Finally, the moiety(s) are mixed with the protein mixture, incubated to promote covalent attachment, and purified to eliminate unreacted moieties.

After labeling a protein ladder with a monoperoxidase and optionally, at least one other chemical moiety, the labeled protein ladder may be separated from any side reaction products and any free hydrolyzed product resulting from normal hydrolysis. In some aspects, size exclusion chromatography (e.g., gel filtration chromatography) using a column of dextran, polyacrylamide, dextran-polyacrylamide, agarose, or the like, and/or dialysis may be used to purify the labeled ladder. A gel filtration media can be selected with a suitable molecular weight cut-off according to the molecular weights of the labeled proteins.

In some aspects, MP-11 labeled protein ladder is purified with a size exclusion column, e.g., spin column. In some instances, the purified labeled protein ladder is diluted in a buffer containing Tris, glycerol and SDS. In some aspects, the buffer, such as a storage buffer, includes 62.5 mM Tris-$H_3PO_4$ (pH 7.5), 30% (v/v) glycerol and 2% SDS.

The labeled protein ladder can be stored in a buffer, e.g., storage buffer. The selected storage buffer can, for example, stabilize the protein ladder, stabilize three functionalities of the protein ladder (visible dyes, fluorescent dyes and chemiluminescence), prevent denaturation, inhibit degradation, or preserve the protein ladder for long-term storage (e.g., up to one year) at various temperatures including room temperature, 4° C., −20° C., and −80° C. The storage buffer can include 50 mM-65 mM Tris, pH 6.8-7.5, 20-40% (v/v) glycerol and 1-3% SDS. In some aspects, the storage buffer contains 62.5 mM Tris-$H_3PO_4$ at pH 7.5, 25% (v/v) glycerol and 5% SDS. In preferred aspects, EDTA, DTT and $NaN_3$ are not present in the storage buffer. The inventors have discovered that storing MP-11 labeled proteins in the presence of DTT, EDTA, $NaN_3$ or any combination thereof reduces (e.g., decreases) the catalytic-like activity of the microperoxidase.

Provided herein is a kit for generating a catalytic protein molecular weight ladder that includes a plurality of purified proteins of different molecular weights (i.e., a protein ladder), mono microperoxidase NHS ester (e.g., mono acetylated MP-11 NHS ester), and a labeling buffer. In some aspects, the labeling buffer is an amine-free buffer, e.g., a buffer that is free or substantially free of amine. In some instances, the labeling buffer is 50 mM sodium phosphate at about pH 7.7-9.0. In some aspects, the kit also contains storage buffer that is free or substantially free of one or more of the following: DTT, EDTA, $NaN_3$, and antibodies with catalytic activity. In other aspects, the kit includes an instruction manual. In certain instances, the buffer optionally comprises 0.1%-1% SDS.

D. Methods of Using Multifunctional Protein Molecular Weight Ladders for Quantitating the Amount of Protein in a Test Sample For detecting multiple proteins in western blotting, it is desirable to use a protein ladder that shows up on digital imaging equipment and also corresponds to signal emitting from target detection. The multifunctional protein molecular weight ladder provided herein is applicable for estimation of at least three molecular weights of target proteins simultaneously or subsequently. Chemiluminescent and fluorescent protein bands at 700 nm and 800 nm can be visualized with instruments equipped with dual-mode detection systems, such as the Odyssey® Fc for NIR fluorescence and chemiluminescence, individual systems, such as the Odyssey® CLx, Odyssey® Sa, CDiGit® blot scanner, and other chemiluminescence imaging systems.

In yet another embodiment, the present invention provides a method for performing a Western blot analysis, the method comprising:
 (a) loading a protein standard comprising a plurality of purified proteins of differing molecular weight, wherein at least a first portion of the purified proteins is covalently labeled with a mono microperoxidase (MP) N-hydroxy succinimidyl (NETS) ester;
 (b) electrophoresing the plurality of proteins to form a separated protein mixture;
 (c) transferring the separated protein mixture to a membrane;
 (d) adding a chemiluminescent substrate to form a chemiluminescent signal; and
 (e) capturing the chemi-signal with a film or an imager.

In some aspects, the membrane is nitrocellulose or PVDF. In some aspects, an unknown protein is loaded with the protein standard.

In some instances, the multifunctional protein ladder is run on a SDS-PAGE polyacrylamide gel, e.g., NuPAGE® Bis-Tris gel with 1× NuPAGE® MES-SDS Running Buffer (Thermo Fisher Scientific, Waltham, Mass.) at 160V, constant voltage for about 55 minutes. The pre-stained proteins of the ladder can be visualized and imaged. The fluorescently labeled proteins can be analyzed using a digital imaging system equipped with fluorescence detectors. Alternatively, the SDS-PAGE gel containing the resolved multifunctional protein ladder can undergo western blotting processing. The proteins can be transferred to a membrane, e.g., a nitrocellulose, PVDF or the like membrane).

For western blotting, the MP-11 labeled proteins of the protein ladder may be detected by reacting the microperoxidase with a suitable substrate, including, but not limited to, a chromogenic substrate (e.g., 3,5-di-t-butyl-catechol (DTBC), 3,3',5,5'-tetramethylbenzidine (TMB), 2,2'-azino-bis(3-ethylbenzothiazoline-6-sulfonic acid) (ABTS), 4-aminoantipyrene (4AAP), 4-chloro-1-naphthol (4CN), 5-bromo-4-chloro-3-indolyl phosphate/nitroblue etrasolium (BCIP/NBT), or diaminobenzidine (DAB)), a chemiluminescent substrate (e.g., luminol, isomers thereof, or derivatives thereof) and a fluorescent substrate (e.g., 4-(N-methylhydrazino)-7-nitro-2,1,3-benzooxadiazole (MNBDH)). In some aspects, a chemiluminescent signal is generated after applying a luminol-based substrate to the MP-11 labeled protein ladder of a western blot. The signal can be detected by digital imaging equipment such as the Odyssey® Fc or similar devices. Optionally, the fluorescence labeled proteins of the protein ladder may be detected using a digital fluorescence detector.

IV. Examples

The following examples are offered to illustrate, but not to limit, the claimed invention.

Example 1. Synthesis of Mono MP-11 NHS Esters

This example illustrates a two-step method for synthesizing mono MP-11 NHS esters (FIG. 1). The inventors have discovered that blocking the first primary amino moiety in MP-11 using sulfo-NHS acetate, in aqueous solution (pH 8.5 phosphate buffer), and at low MP-11 concentration improves conjugation efficiency and eliminates MP-11 aggregation. The N-acetylated MP-11 was purified in the second step of the reaction. Purification of N-acetylated MP-11 (pH=2-5) did not inhibit peroxidase-like activity of the modified MP-11. The synthesis of MP-11 NHS ester is performed in organic solvent. However, the unmodified MP-11 is not soluble in such solvents. N-acetylating MP-11 increases the solubility of MP-11, and thus, the mono MP-11 NHS ester can be prepared in organic solvent by using a homobifunctional NHS ester. Mono MP-11 NHS ester retained peroxidase-like activity, resulting in less aggregation, high purity and better yield.

Example 2. Methods for Labeling Protein Ladders Using Mono MP-11 NHS Esters

The protein molecular markers, such as unstained and pre-stained protein ladders were labeled with mono MP-11 NHS ester as described above. The protein ladders included those containing one or more molecular weight proteins of about 260 kDa, 160 kDa, 140 kDa, 130 kDa, 100 kDa, 90 kDa, 70 kDa, 55 kDa, 50 kDa, 40 kDa, 38 kDa, 35 kDa, 30 kDa, 25 kDa, 15 kDa, 10 kDa, 8 kDa, and any combination thereof. Additionally, protein ladders labeled with a fluorescent moiety, such as a near-infrared dye that can be visualized by SDS-PAGE or western blotting using a fluorescent detection instrument, were labeled with mono MP-11 ester. Total protein concentration of the protein ladder was estimated in the range of 0.25 mg/ml to 1 mg/ml. The mean molecular weight of protein ladder was estimated. Protein concentration, reaction time, molar ratio between mono MP-11 NHS ester and proteins was optimized for the labeling reaction.

The labeled protein markers were resolved by standard gel electrophoresis. NIR fluorescence was detected using the Odyssey® infrared imaging system (LI-COR). The protein ladder was also transferred from the gel to a blotting membrane using standard western blotting methods. A chemiluminescent substrate was applied to the blot and digitally imaged with a CCD camera system such as the Odyssey® Fc (LI-COR).

Figure 2A:
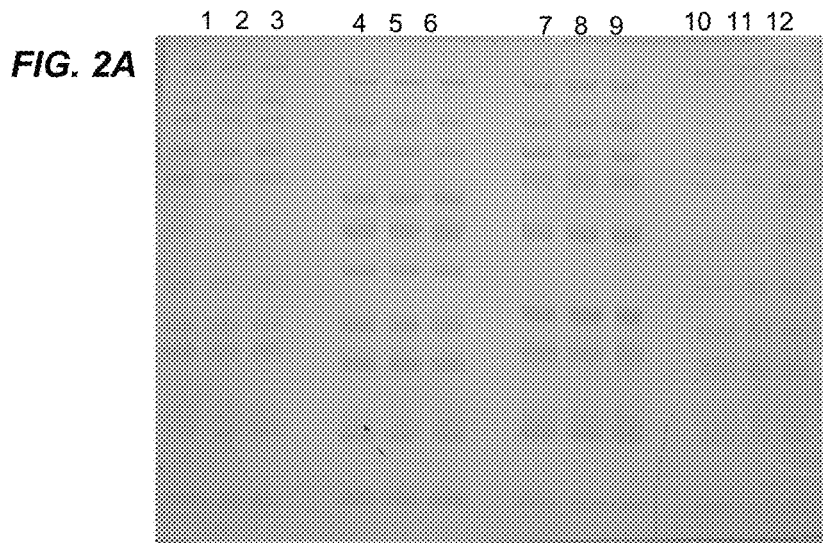
FIGS. 2A-2C show an exemplary embodiment of a multifunctional marker described herein. The protein marker ladder contains pre-stained proteins with visible dyes (FIG. 2A), chemiluminescent signal (FIG. 2B) and IR fluorescent moieties (FIG. 2C).
Figure 2B:
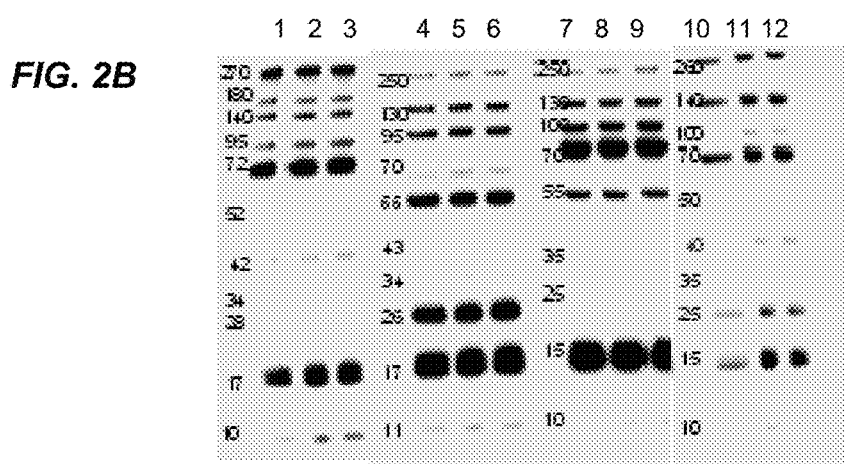
Figure 2C:
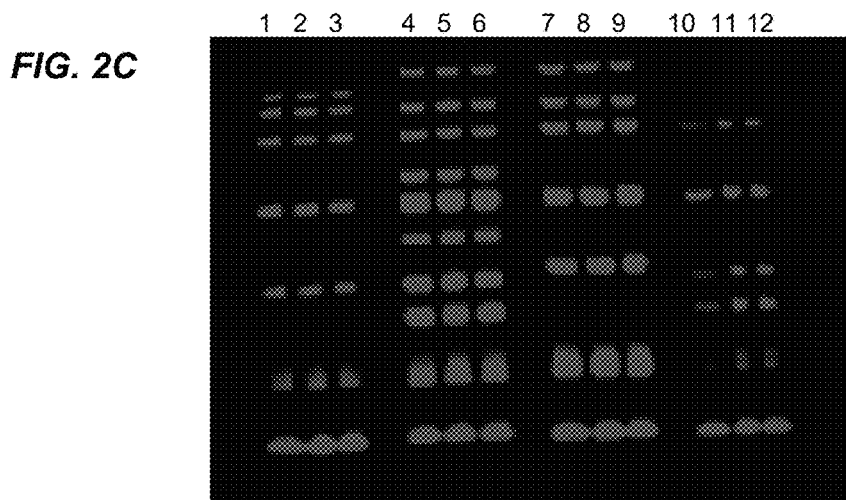

The protein markers all displayed pre-stained properties, peroxidase-like activity and fluorescent properties. As shown in the FIGS. 2A-C, the multifunctional markers show discrete chemiluminescent protein bands upon developing with luminol-based chemiluminescence substrates.

Figure 3A:
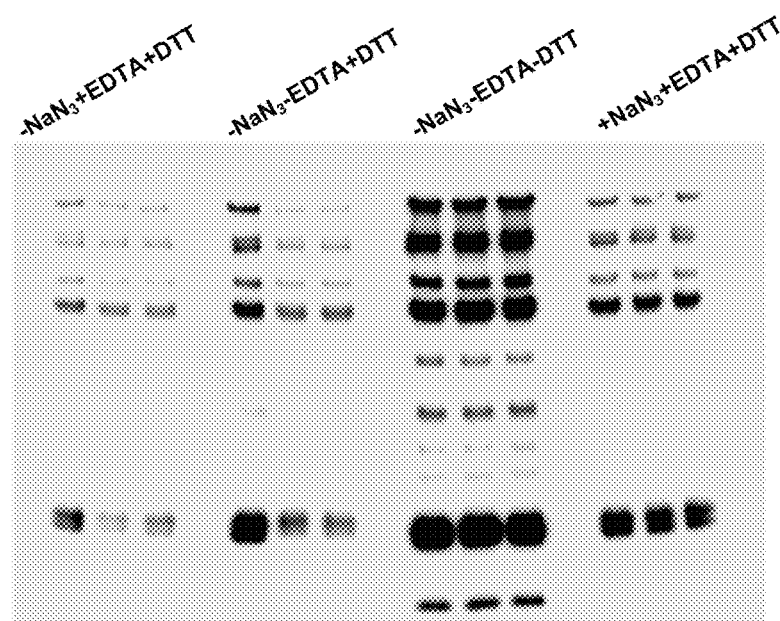
FIGS. 3A and 3B show the stability of an exemplary embodiment of a multifunctional marker described herein. The marker ladder stored in DTT, NaN$_3$ and EDTA-free buffer retains its peroxidase-like activity.
Figure 3B:
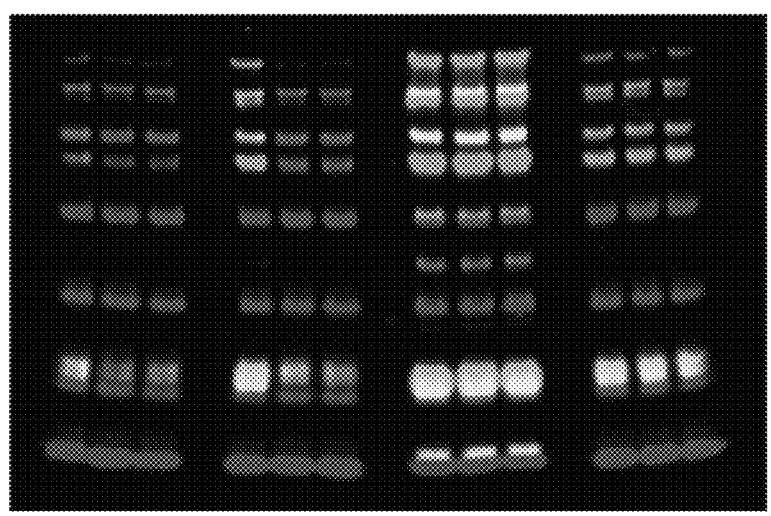

Additives, such as EDTA, DTT and $NaN_3$ are commonly included in storage buffers for molecular weight markers because they can increase long term stability. However, EDTA, DTT and $NaN_3$ can complex with iron in the heme group and may affect the catalytic activity of MP-11. $NaN_3$ and DTT may also destroy intermediates of super oxides radicals in the chemiluminescence reaction. To test the stability of the multifunctional protein ladder in the presence of standard additives, the ladders were stored in various buffers including those containing EDTA, DTT and $NaN_3$. The storage buffer was composed of 62.5 mM Tris-$H_3PO_4$ (pH 7.5), 2% SDS and 25% glycerol. The peroxidase-like activity was decreased when the protein markers were stored in a buffer containing DTT, $NaN_3$ and/or EDTA. As shown in FIG. 3A-B, the peroxidase-like activity disappeared after two days at room temperature (about 20-25° C.) in storage buffer containing DTT, $NaN_3$ and EDTA. However, the protein ladders stored in DTT-, $NaN_3$- and EDTA-free buffer retained its peroxidase-like activity.

Figure 4A:
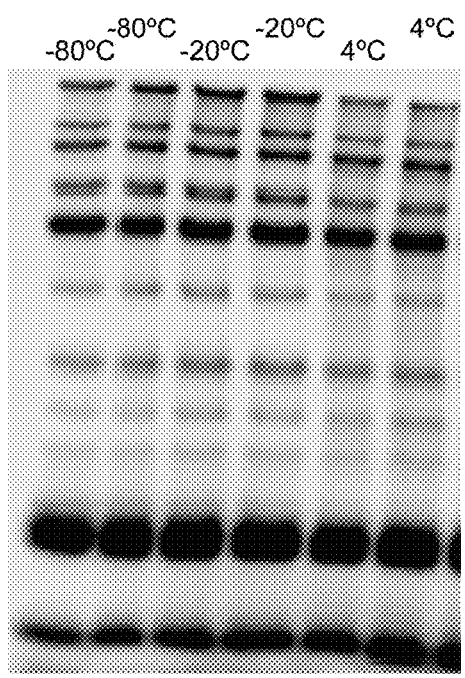
FIGS. 4A and 4B show the stability of two multifunctional protein ladders labeled with mono MP-11 ester and stored at −80° C., −20° C. and 4° C.
Figure 4B:
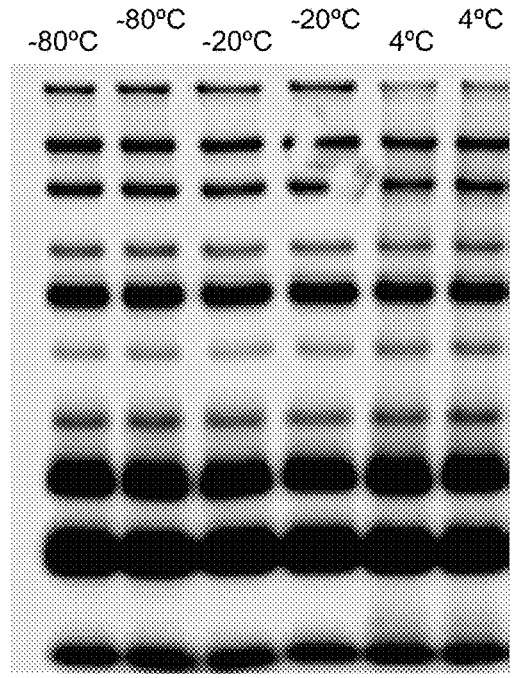

The stability of the multifunctional ladder stored in DTT-, $NaN_3$- and EDTA-free buffer was evaluated at different storage temperatures. FIGS. 4A-B show that the protein ladders (a pre-stained protein ladder in FIG. 4A; a dual function protein ladder with pre-stained proteins and IR dye coupled proteins in FIG. 4B) were stable after 5-6 months when stored at −80° C., −20° C. and 4° C.

Example 3. Methods for Conjugating Moieties to a Mixture of Proteins

This example illustrates a method for making a multifunctional protein ladder that includes proteins labeled with IRDye® 800CW (Cat. No. 830-08038, LI-COR, Lincoln, Nebr.). The method comprises the steps of: (1) dialyzing the pre-stained protein molecular weight marker in sodium phosphate buffer, (2) determining the number of molar equivalents of the IRDye® 800CW to be added based on the mean molecular weight of the protein ladder, (3) performing the labeling reaction, and (4) removing unreacted IRDye® 800CW after the reaction is complete.

The protein molecular weight marker was dialyzed in a hydrated 2000 MWCO dialysis cassette in 50 mM sodium phosphate buffer, pH 8.5 for overnight (or at least 16 hours) at ambient temperature.

The amount (mass) of the protein molecular weight marker in mg was determined by multiplying the concentration supplied by the manufacturer by the volume in ml of the marker to be labeled. To calculate the amount of IRDye® needed to label the dialyzed marker, the following equation was used:

$$\frac{\text{Protein Marker Mass (mg)}}{\text{Average MW Protein Marker}} \times \text{Dye Molar Equivalents} \times \text{Dye MW} = \text{Dye Needed (mg)}$$

MW=Molecular Weight (g/mole)

The appropriate volume of dye needed for the labeling reaction was added to the dialyzed protein marker and vortexed gently but thoroughly. The labeling reaction was incubated at about 20° C. for 2-4 hours and protected from light. Optionally, the reaction is then stored overnight (12-24 hours) at 4° C. protected from light to allow the reaction to go to completion and the residual dye to hydrolyze. Unre- Example 4. A Pre-stained Chemiluminescent Protein Ladder A pre-stained chemiluminescent protein ladder was designed to provide a ladder of convenient and consistent protein sizes (8-250 kDa) for use with polyacrylamide gels and on Western membranes where chemiluminescent detection is used. The Ladder offers both pre-stained and chemiluminescent functionalities. The Ladder is suitable for use with film and a variety of chemiluminescent substrates and can be detected on Odyssey® Fc, CDiGit® Blot Scanner, and other imaging modalities capable of chemiluminescent detection. In gels, the Ladder can be used to visualize progress of the protein separation during electrophoresis and to determine the molecular weight of unknown proteins based on their relative mobility. In blotting applications, the Ladder can be used to monitor protein transfer and as a reference to determine the molecular weight of proteins of interest.

Figure 5:
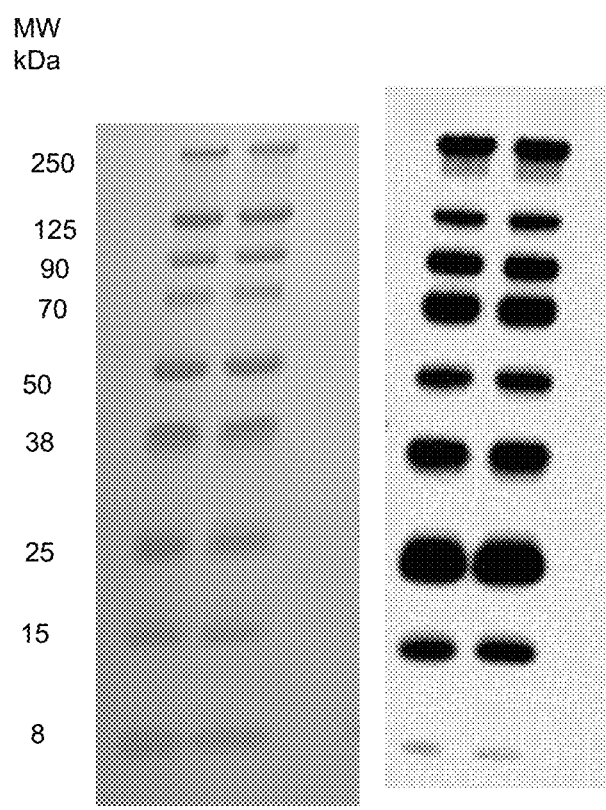
FIG. 5 shows representative visible (left) and chemiluminescent (right) images of a chemiluminescent protein ladder resolved on a 4-12% Bis-Tris Gel and transferred to nitrocellulose via a wet tank transfer.

FIG. 5 shows representative visible (left) and chemiluminescent (right) images of the chemiluminescent protein Ladder resolved on a 4-12% bis-Tris gel and transferred to a nitrocellulose membrane via wet tank transfer. The membrane was exposed to WesternSure ECL Substrate (LI-COR, P/N 926-80100) and scanned on a C-DiGit Blot Scanner for 12 minutes.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A compound having the formula:

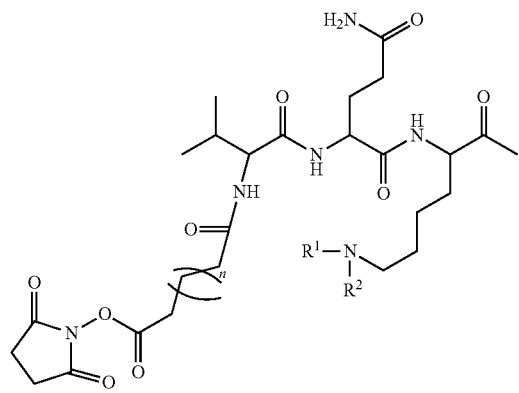

-continued

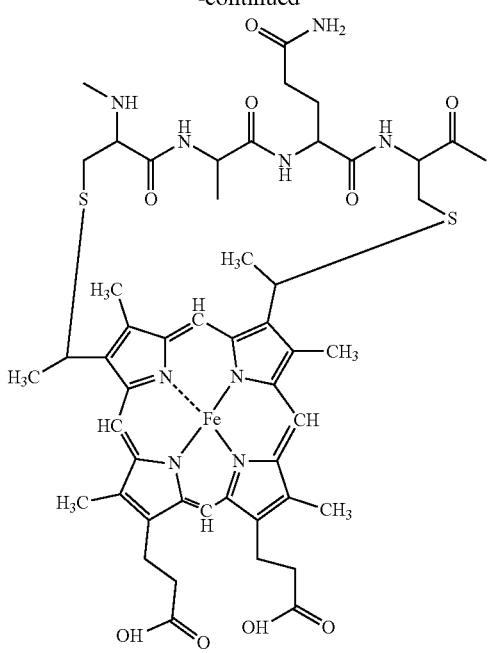

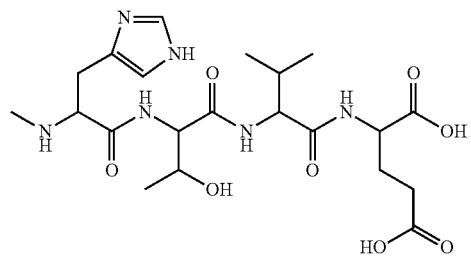

wherein n is 0-10 and;

$R^1$ and $R^2$ are each independently a member selected from the group consisting of hydrogen and an acetyl (Ac), with the proviso that one of $R^1$ or $R^2$ is acetyl and one of $R^1$ or $R^2$ is hydrogen.

2. The compound of claim 1, wherein n is 4, $R^1$ is hydrogen and $R^2$ is acetyl.

3. The compound of claim 1, wherein n is 4, $R^1$ is acetyl and $R^2$ is hydrogen.

4. A kit for preparing the protein standard, the kit comprising a plurality of purified proteins of differing molecular weight, a compound, and a labeling buffer, wherein the compound has the formula:

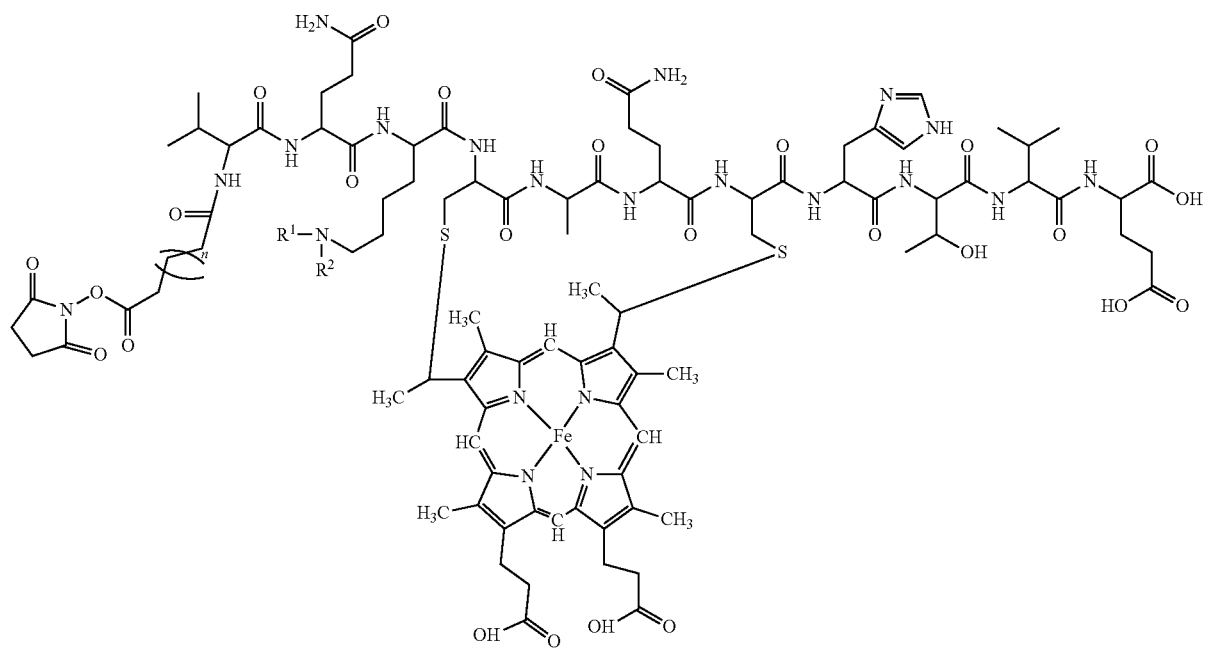

wherein n is 0-10 and;

R[1] and R[2] are each independently a member selected from the group consisting of hydrogen and an acetyl (Ac), with the proviso that one of R[1] or R[2] is acetyl and one of R[1] or R[2] is hydrogen.

5. The kit of claim 4, wherein the labeling buffer is an amine-free buffer.

6. The kit of claim 4, wherein the labeling buffer contains SDS.

7. The kit of claim 4, further comprising a storage buffer.

8. The kit of claim 4, wherein the storage buffer is substantially free of DTT, EDTA and NaN$_3$.

9. A method for preparing a multifunctional protein standard comprising a plurality of purified proteins labeled with at least two chemical moieties selected from the group consisting of a visible dye moiety, a catalytic moiety, a fluorescent dye moiety, a chemiluminescent moiety, and a combination thereof, said method comprising:
  (a) determining the optimum number of molar equivalents of the at least two chemical moieties based on the average molecular weight of the plurality of purified proteins when labeled individually;
  (b) preparing the plurality of purified proteins in a buffer amenable to the conjugation chemistries of the at least two chemical moieties; and
  (c) incubating the at least two chemical moieties and the plurality of purified proteins under conditions such that the at least two chemical moieties covalently attach to the proteins to produce the multifunctional protein standard; wherein one of the at least two chemical moieties is the catalytic moiety, wherein the catalytic moiety is a monoacetylated MP-11 NHS ester having the formula:

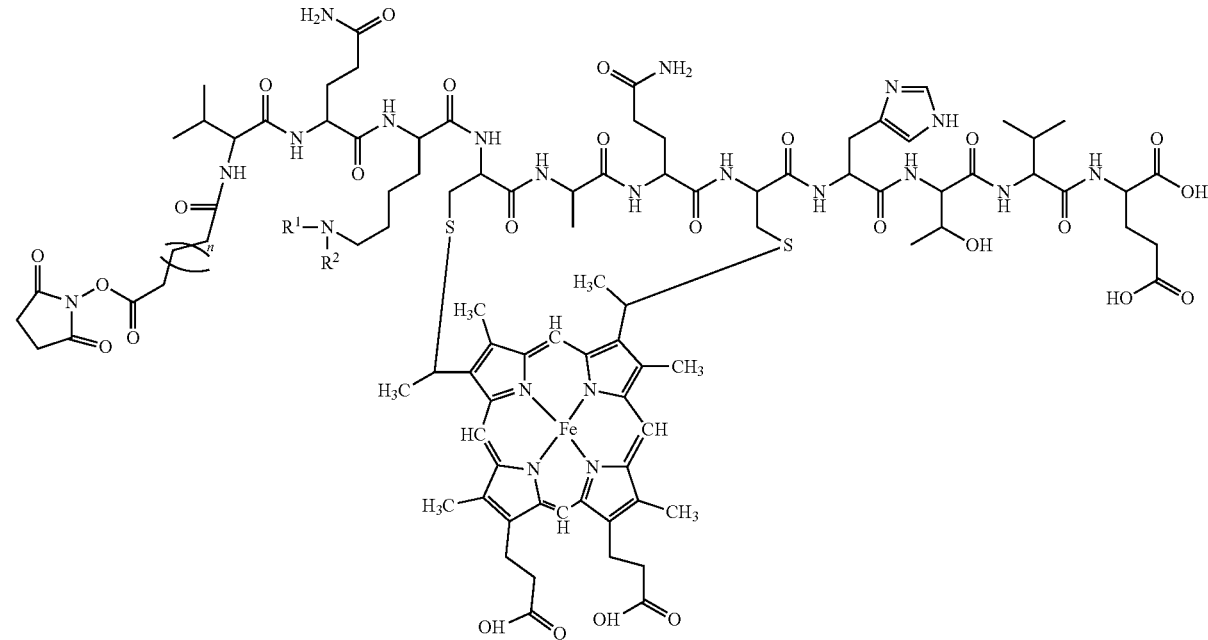

Wherein n is 1-10 and;

R[1] and R[2] are each independently a member selected from the group consisting of hydrogen and an acetyl (Ac), with the proviso that one of R[1] or R[2] is acetyl and one of R[1] or R[2] is hydrogen.

10. The method of claim 9, further comprising purifying the multifunctional protein standard.

11. The method of claim 9, wherein purifying the multifunctional protein standard comprises size exclusion chromatography or dialysis.

12. The method of claim 9, wherein incubating the at least two chemical moieties and the plurality of purified proteins comprises simultaneously conjugating the chemical moieties to the proteins.

13. The method of claim 9, wherein incubating the at least two chemical moieties and the plurality of purified proteins comprises sequentially conjugating the chemical moieties, wherein the monoacetylated MP-11 NHS ester is conjugated to the proteins after the proteins are conjugated to a chemical moiety without having an NHS ester.

14. The method of claim 9, wherein incubating the at least two chemical moieties and the plurality of purified proteins comprises sequentially conjugating the chemical moieties, wherein the order of conjugating is from the least to most molar equivalents needed for each chemical moiety.

15. The method of claim 9, wherein at least two purified proteins of the multifunctional protein standard are labeled with the catalytic moiety and the visible dye moiety.

16. A method for performing a Western blot analysis, the method comprising
  (a) loading a protein standard comprising a plurality of purified proteins of differing molecular weight, wherein at least a first portion of the purified proteins is covalently labeled with a mono microperoxidase (MP) N-hydroxy succinimidyl (NHS) ester having the formula:

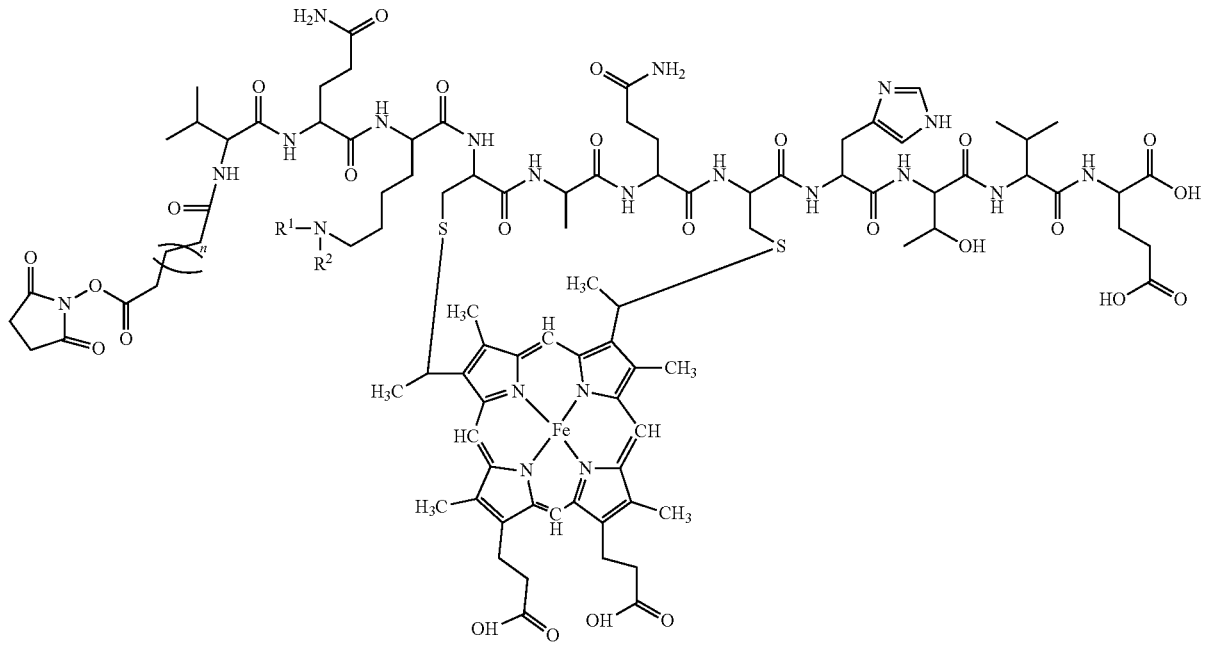

wherein n is 0-10 and;
R[1] and R[2] are each independently a member selected from the group consisting of hydrogen and an acetyl (Ac), with the proviso that one of R[1] or R[2] is acetyl and one of R[1] or R[2] is hydrogen;

(b) electrophoresing the plurality of proteins to form a separated protein mixture;
  (c) transferring the separated protein mixture to a membrane;
  (d) adding a chemiluminescent substrate to form a chemiluminescent signal; and
  (e) capturing the chemi-signal with a film or an imager.

* * * * *